United States Patent
Matsui et al.

(10) Patent No.: US 9,642,666 B2
(45) Date of Patent: May 9, 2017

(54) ABLATION METHOD

(71) Applicant: OLYMPUS CORPORATION, Tokyo (JP)

(72) Inventors: Shoichi Matsui, Sagamihara (JP); Kenichi Nishina, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 320 days.

(21) Appl. No.: 14/459,373

(22) Filed: Aug. 14, 2014

(65) Prior Publication Data
US 2016/0045245 A1 Feb. 18, 2016

(51) Int. Cl.
| | |
|---|---|
| *A61B 18/02* | (2006.01) |
| *A61B 18/04* | (2006.01) |
| *A61B 18/00* | (2006.01) |
| *A61B 17/00* | (2006.01) |
| *A61B 5/00* | (2006.01) |
| *A61B 5/01* | (2006.01) |

(Continued)

(52) U.S. Cl.
CPC ............ *A61B 18/02* (2013.01); *A61B 18/04* (2013.01); *A61B 5/0008* (2013.01); *A61B 5/01* (2013.01); *A61B 5/015* (2013.01); *A61B 2017/00022* (2013.01); *A61B 2017/00084* (2013.01); *A61B 2017/00088* (2013.01); *A61B 2018/00482* (2013.01); *A61B 2018/00577* (2013.01); *A61B 2018/00642* (2013.01); *A61B 2018/00714* (2013.01); *A61B 2018/00773* (2013.01); *A61B 2018/00791* (2013.01); *A61B 2018/00797* (2013.01); *A61B 2018/00815* (2013.01); *A61B 2018/00821* (2013.01); *A61B 2018/00904* (2013.01); *A61B 2018/00982* (2013.01); *A61B 2018/0293* (2013.01); *A61B 2018/1465* (2013.01); *A61B 2090/3784* (2016.02); *A61B 2560/0271* (2013.01)

(58) Field of Classification Search
None
See application file for complete search history.

(56) References Cited

U.S. PATENT DOCUMENTS

| | | | |
|---|---|---|---|
| 7,182,761 B2 * | 2/2007 | Garabedian | A61B 18/1477 606/41 |
| 2002/0128650 A1 * | 9/2002 | McClurken | A61B 18/1442 606/48 |

FOREIGN PATENT DOCUMENTS

| | | |
|---|---|---|
| JP | 08-308853 A | 11/1996 |
| JP | 2013-240600 A | 12/2013 |

* cited by examiner

*Primary Examiner* — Ronald Hupczey, Jr.
*Assistant Examiner* — Jennifer Le
(74) *Attorney, Agent, or Firm* — Scully, Scott, Murphy & Presser, P.C.

(57) ABSTRACT

An ablation method according to the present invention includes: a step I of observing a target region in a tissue of a subject and a conservation region that should not be ablated, the conservation region being adjacent to the ablation target region, using an observation unit; a step II of placing a thermal monitoring instrument that deforms if a temperature thereof exceeds a predetermined temperature, in a boundary between the ablation target region and the conservation region under the observation using the observation unit; a step III of heating the ablation target region using an ablation instrument while observing the ablation target region using the observation unit; and a step IV of stopping the heating at a stage where deformation of the thermal monitoring instrument is confirmed.

2 Claims, 15 Drawing Sheets

(51) Int. Cl.
*A61B 18/14* (2006.01)
*A61B 90/00* (2016.01)

ABLATION METHOD

BACKGROUND OF THE INVENTION

1. Field of the Invention

The present invention relates to an ablation method in which a tissue of a subject is heated or cooled.

2. Description of the Related Art

Thermal treatment called ablation in which a tissue of a living object such as a human body, which is a subject, is heated or cooled to degenerate the tissue or cells is known.

As an example of the type of ablation in which a tissue is heated, a method in which a tissue is subjected to, e.g., application of a high-frequency voltage such as microwave or radio wave, focused ultrasound irradiation or laser irradiation to make the tissue produce heat is known. Also, as an example of ablation in which a tissue is cooled, a method in which a tissue is cooled and frozen using a low-temperature liquid such as liquid nitrogen and vaporization phenomenon of such liquid is known.

As an example of ablation, Japanese Patent Application Laid-Open Publication No. 8-308853 discloses a treatment method in which tumor cells in a tissue are heated and thereby killed.

It has been proposed that where a tissue is heated or cooled by means of ablation, thermography or a thermocouple is used to monitor change in temperature of a target tissue and a tissue in the periphery thereof.

SUMMARY OF THE INVENTION

An ablation method according to an aspect of the present invention includes: a step I of observing an ablation target region in a tissue of a subject and a conservation region that should not be ablated, the conservation region being adjacent to the ablation target region, using observation means; a step II of placing a heat monitoring instrument that deforms if a temperature thereof exceeds a predetermined temperature, in a boundary between the ablation target region and the conservation region under the observation using the observation means; a step III of heating the ablation target region using an ablation instrument while observing the ablation target region using the observation means; and a step IV of stopping the heating at a stage where deformation of the heat monitoring instrument is confirmed.

Also, an ablation method according to another aspect of the present invention includes: a step I of observing an ablation target region in a tissue of a subject and a conservation region that should not be ablated, the conservation region being adjacent to the ablation target region, using observation means; a step II of placing a heat monitoring instrument that deforms if a temperature thereof falls below a predetermined temperature, in a boundary between the ablation target region and the conservation region under the observation using the observation means; a step III of cooling the ablation target region using an ablation instrument while observing the ablation target region using the observation means; and a step IV of stopping the cooling at a stage where deformation of the heat monitoring instrument is confirmed.

DETAILED DESCRIPTION OF THE PREFERRED EMBODIMENTS

Preferred embodiments of the present invention will be described below with reference to the drawings. Note that each figure used for the below description illustrates respective components with different scales so that the respective components have sizes enough to be identified on the figure, and in the present invention, the counts of the components, the shapes of the components, the ratios in size among the components and the relative positional relationships among the respective components are not limited only to those described in these figures.

First Embodiment

An ablation method according to the present embodiment is a procedure for subjecting a living object such as a human body, which is a subject, to ablation in which a predetermined tissue is heated or cooled.

In the present invention, the method, the object, and the part that is the target, of ablation are not specifically limited. As examples of the ablation method in which a tissue of a subject is heated, methods in which a tissue is made to generate heat such as a method in which a high-frequency voltage such as microwave or radio wave is applied to a tissue, a method in which a tissue is irradiated with focused ultrasound and a method in which a tissue is irradiated with laser are known. Also, a method in which saline having a temperature that is higher than that of an internal environment of a subject is injected to a tissue to heat the tissue is known. Also, as an example of the ablation methods in which a tissue of a subject is cooled, a method in which a tissue is cooled and frozen using a low-temperature liquid such as liquid nitrogen and vaporization phenomenon of such liquid is known.

Also, as objects of ablation in which a tissue of a subject is heated, for example, killing or reducing a malignant tumor such as pancreas cancer, liver cancer, kidney cancer, lung cancer, prostate cancer or malignant lymphoma and killing or reducing a benign tumor such as uterine fibroid or endometriosis are known.

Figure 1:
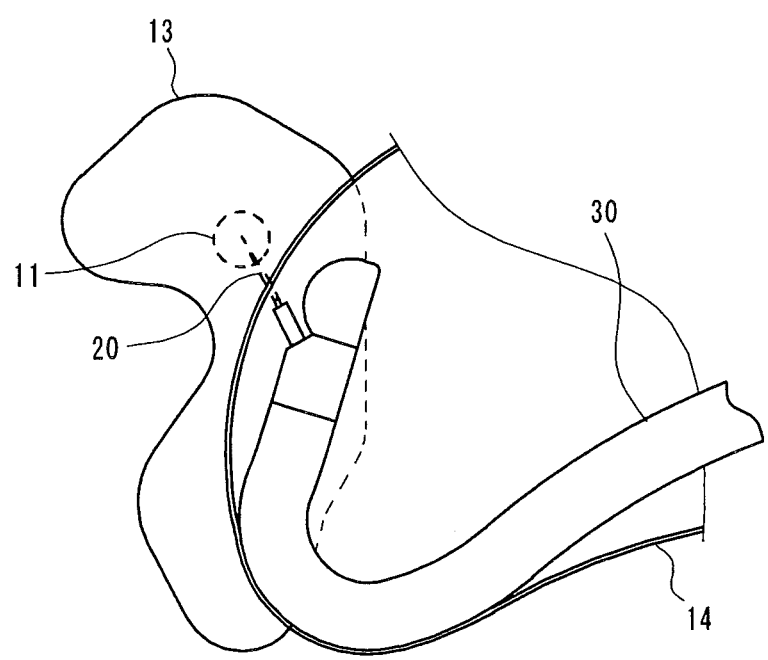
FIG. 1 is a schematic diagram illustrating a target region of an ablation method according to a first embodiment.

In the present embodiment, as an example, as illustrated in FIG. 1, a target region 11 including a tissue of a part of a pancreas 13 of a human body, which is a subject, is heated using an ablation instrument 20, which is heating means. In the present embodiment, the target region 11 is a region in which a tissue to be heated to a temperature exceeding a predetermined temperature Th by operation of the ablation instrument 20 exists. For example, the target region 11 includes all or a part of tumor cells existing in the pancreas 13.

The ablation instrument 20 heats the tissue in the ablation target region 11 by applying a high-frequency voltage such as microwave or radio wave to the tissue. Hereinafter, the ablation target region 11 is simply referred to as the target region 11. Since the specific configuration of the ablation instrument 20 is known, detailed description thereof will be omitted. In the present embodiment, the ablation instrument 20 is brought to the target region 11 using an ultrasound endoscope 30 inserted inside a stomach 14. Also, in ablation according to the present embodiment, a later-described heat monitoring instrument 1, which is not illustrated in FIG. 1, is used.

First, an example of a configuration of the heat monitoring instrument 1 will be described. The heat monitoring instrument 1 is an apparatus including an insertion portion 2 that can be inserted into a tissue of a subject and also including a part that deforms if a temperature thereof exceeds a predetermined temperature or falls below a predetermined temperature, as a part of the insertion portion 2. Note that the heat monitoring instrument 1 may be of a type including a part that deforms if a temperature thereof deviates to the high temperature side or the low temperature side from a predetermined temperature range in an insertion portion 2.

If ablation is of the type that heats the target region 11 as in the present embodiment, the insertion portion 2 of the heat monitoring instrument 1 includes a part that deforms if a temperature thereof exceeds a predetermined temperature Th. Note that if ablation is of the type that cools the target region 11, a heat monitoring instrument 1 including an insertion portion 2 including a part that deforms if a temperature thereof falls below a predetermined temperature Tl is used, which will be described later as a second embodiment.

Figure 2:
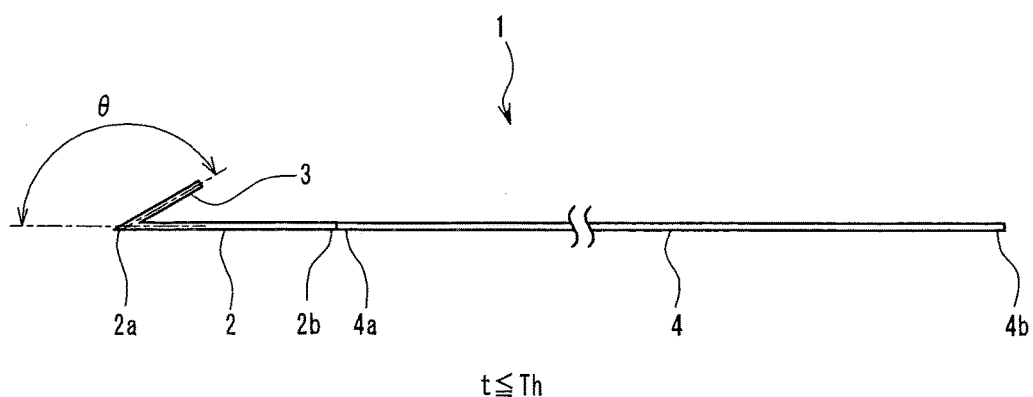
FIG. 2 is a diagram illustrating a configuration of a heat monitoring instrument according to the first embodiment.

FIG. 2 illustrates an example of the heat monitoring instrument 1 according to the present embodiment. The heat monitoring instrument 1 includes the insertion portion 2, a locking portion 3 provided in the insertion portion 2, and a linear member 4 coupled to the insertion portion 2.

The linear member 4 is an elongated linear member formed of, e.g., a metal, a resin or a fiber. A shape and a material of the linear member 4 only need to be those that can provide a member that endures a tensile force of a predetermined magnitude (a pulling force applied in a longitudinal direction) and are not specifically limited. For example, the linear member 4 may be of a type that upon application of a compressive force thereto in the longitudinal direction, easily buckles and deforms like a string. Also, for example, the linear member 4 may be of a type that, even upon application of a compressive force thereto in the longitudinal direction, does not buckle until the compressive force exceeds a predetermined value like a wire. In other words, the linear member 4 may be of a type that transmits a compressive force or of a type that does not transmit a compressive force in the longitudinal direction as long as such member transmits a tensile force in the longitudinal direction.

Note that although the illustrated linear member 4 of the present embodiment has a fixed thickness in the longitudinal direction, the linear member 4 may have a shape whose cross section varies along the longitudinal direction. Also, the linear member 4 does not need to be formed of a single member, and the linear member 4 may be formed of a plurality of members. For example, the linear member 4 may be of a type in which a plurality of members exist in a same cross section like a twist yarn or may also be of a type in which a plurality of members are joined in a longitudinal direction like a chain.

A distal end portion 4a, which is one end of the linear member 4, is coupled to the insertion portion 2. Note that the linear member 4 and the insertion portion 2 may be integrally formed by a single member.

The insertion portion 2 is a part that can be inserted into a tissue of a living object such as a human body, which is a subject. In the insertion portion 2, a locking portion 3 is provided. In the insertion portion 2, a shape of the locking portion 3 when the locking portion 3 has a temperature that is equal to or below a predetermined temperature Th and that of when the locking portion 3 has a temperature in a predetermined temperature range exceeding the predetermined temperature Th are different from each other as described later. In other words, the insertion portion 2 has a part that deforms when a temperature thereof is raised from a temperature that is equal to or below the predetermined temperature Th to a temperature exceeding the predetermined temperature Th.

Here, the insertion portion 2 only needs to be configured so as to deform when the insertion portion 2 is heated from a temperature that is equal or to below the predetermined temperature Th to a temperature exceeding the predetermined temperature Th, and does not need to deform when the temperature is lowered from a temperature exceeding the predetermined temperature Th to a temperature that is equal to or below the predetermined temperature Th. In other words, deformation according to change in temperature of the insertion portion 2 may be irreversible.

When the insertion portion 2 is inserted inside a tissue of a subject and a temperature of the insertion portion 2 is equal to or below the predetermined temperature Th, the locking portion 3 engages with a surrounding tissue. Here, if a force is applied to the insertion portion 2 in a direction in which the insertion portion 2 is removed from the inside of the tissue, the locking portion 3 generates a resistive force that keeps the insertion portion 2 inside the tissue against that force.

Accordingly, when the insertion portion 2 is inserted inside a tissue and the temperature of the insertion portion 2 is equal to or below the predetermined temperature Th, even if a tensile force is applied to the linear member 4 by pulling the proximal end side of the linear member 4, the insertion portion 2 remains inside the tissue because the locking portion 3 engages with the tissue. It should be understood that if an excessive tensile force that largely deforms, or destroys, the tissue is applied to linear member 4, the insertion portion 2 comes off.

Then, when the insertion portion 2 is inserted inside a tissue of a living body and the insertion portion 2 is heated from a temperature that is equal to or below the predetermined temperature Th to a temperature exceeding the predetermined temperature Th, the locking portion 3 deforms, losing the locking function, whereby the locking portion 3 and the tissue are disengaged.

Accordingly, when the insertion portion 2 is inserted inside the tissue and the insertion portion 2 is heated to a temperature exceeding the predetermined temperature, the insertion portion 2 moves in a direction in which the insertion portion 2 is removed from the inside of the tissue by pulling the proximal end side of the linear member 4 to apply a tensile force to the linear member 4.

Figure 3:
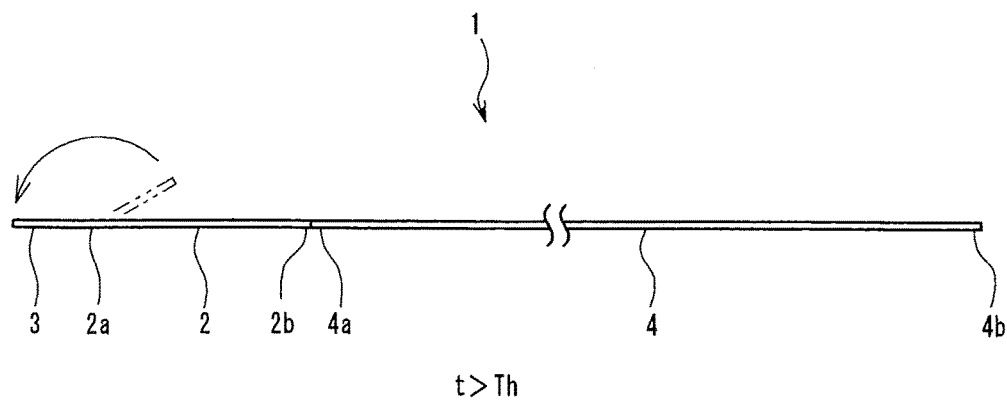
FIG. 3 is a diagram illustrating a state in which an insertion portion of the heat monitoring instrument according to the first embodiment is deformed.

Next, specific configurations of the insertion portion 2 and the locking portion 3 will be described. FIG. 2 illustrates a case where a temperature t of the insertion portion 2 is equal to or below the predetermined temperature Th. FIG. 3 illustrates a case where the temperature t of the insertion portion exceeds the predetermined temperature Th.

As illustrated in FIG. 2, the insertion portion 2 according to the present embodiment includes a linear member. In a distal end portion 2a, which is one end of the insertion portion 2, the locking portion 3 is provided. Also, a proximal end portion 2b, which is the other end of the insertion portion 2, is coupled to the distal end portion 4a of the linear member 4. The insertion portion 2 of the present embodiment is formed of a shape-memory alloy that deforms when the shape-memory alloy is heated to a temperature exceeding the predetermined temperature Th.

If the temperature of the insertion portion 2 is equal to or below the predetermined temperature Th, as illustrated in FIG. 2, the locking portion 3 has a shape in which the distal end portion 2a of the insertion portion 2 including a linear shape-memory alloy is flexed.

More specifically, as indicated by symbol 8 in FIG. 2, the locking portion 3 has a shape in which the insertion portion 2 is flexed by 90 degrees or more at a position that is a predetermined distance from a distal end of the insertion portion 2. In other words, the locking portion 3 has a hook-like shape when the temperature of the insertion portion 2 is equal to or below the predetermined temperature Th. Such shape of the locking portion 3 is referred to as, e.g., a barb in an arrowhead or a fishhook.

Therefore, when the insertion portion 2 is inserted inside a tissue of a living object such as a human body, which is a subject, and the temperature of the insertion portion 2 is equal to or below the predetermined temperature Th, the insertion portion 2 including the locking portion 3 having a hook-like shape engages with a surrounding tissue.

Note that although in the present embodiment illustrated, the flexed portion of the locking portion 3 has a rough V shape, the flexed portion may have a more-rounded shape with a larger radius of curvature.

When the insertion portion 2 is heated from a temperature that is equal to or below the predetermined temperature Th to a temperature exceeding the predetermined temperature Th, as illustrated in FIG. 3, the insertion portion 2 deforms so as to cancel the flexure of the locking portion 3. In other words, in a state in which the insertion portion 2 is heated to a temperature exceeding the predetermined temperature Th and thereby deforms, the locking portion 3 extends along the longitudinal direction of the insertion portion 2 and the insertion portion 2 thus extends in a linear fashion.

Therefore, when the insertion portion 2 is inserted inside a tissue of a living object such as a human body, which is a subject, and the insertion portion 2 is heated from a temperature that is equal to or below the predetermined temperature Th to a temperature exceeding the predetermined temperature Th, the hook-like insertion portion 2 deforms into a linear shape and thereby disengages from the tissue.

Here, a value of the predetermined temperature Th is not specifically limited and arbitrarily set according to a condition for using the heat monitoring instrument 1. In the present embodiment, as an example, the predetermined temperature Th is a value exceeding a temperature at which tumor cells existing in the pancreas 13 are killed. For example, the predetermined temperature Th is in a range of from 42° C. to 45° C. Note that the predetermined temperature Th may be lower than 42° C. and may also exceed 45° C.

When the heat monitoring instrument 1 having the above-described configuration is used, first, the insertion portion 2 is inserted into a tissue of a subject, and then the proximal end side of the linear member 4 is pulled to apply a force in the direction in which the insertion portion 2 is removed from the inside of the tissue. If the temperature of the insertion portion 2 is equal to or below the predetermined temperature Th, the locking portion 3 has a shape that engages with the tissue and thus the insertion portion 2 does not come away from the tissue.

When the insertion portion 2 is heated to a temperature exceeding the predetermined temperature Th, the insertion portion 2 deforms and thereby disengages from the tissue, the insertion portion 2 moves in the direction in which the insertion portion 2 comes away from the tissue, according to a tensile force applied to the linear member 4. In other words, if the temperature of the insertion portion 2 exceeds the predetermined temperature Th, the tensile force that can be applied to the linear member 4 decreases.

As described above, in the present embodiment, the insertion portion 2 of the heat monitoring instrument 1 is inserted into a tissue and then a tensile force is applied to the linear member 4 and change in the tensile force is observed, enabling a user to check whether or not deformation of the insertion portion 2 occurs. Then, recognizing deformation of the insertion portion 2 means that the temperature of the insertion portion 2 exceeds the predetermined temperature Th.

Note that the method for applying a tensile force to the linear member 4 after insertion of the insertion portion 2 of the heat monitoring instrument 1 into a tissue is not specifically limited, and the proximal end portion 4b of the linear member 4 that extends out of the subject may be pulled by a surgeon for the ablation or an assistant for the surgeon via fingers thereof or the proximal end portion 4b of the linear member 4 may be pulled by an apparatus. Also, the proximal end portion 4b of the linear member 4 may be pulled by, e.g., forceps inside the subject.

Figure 4:
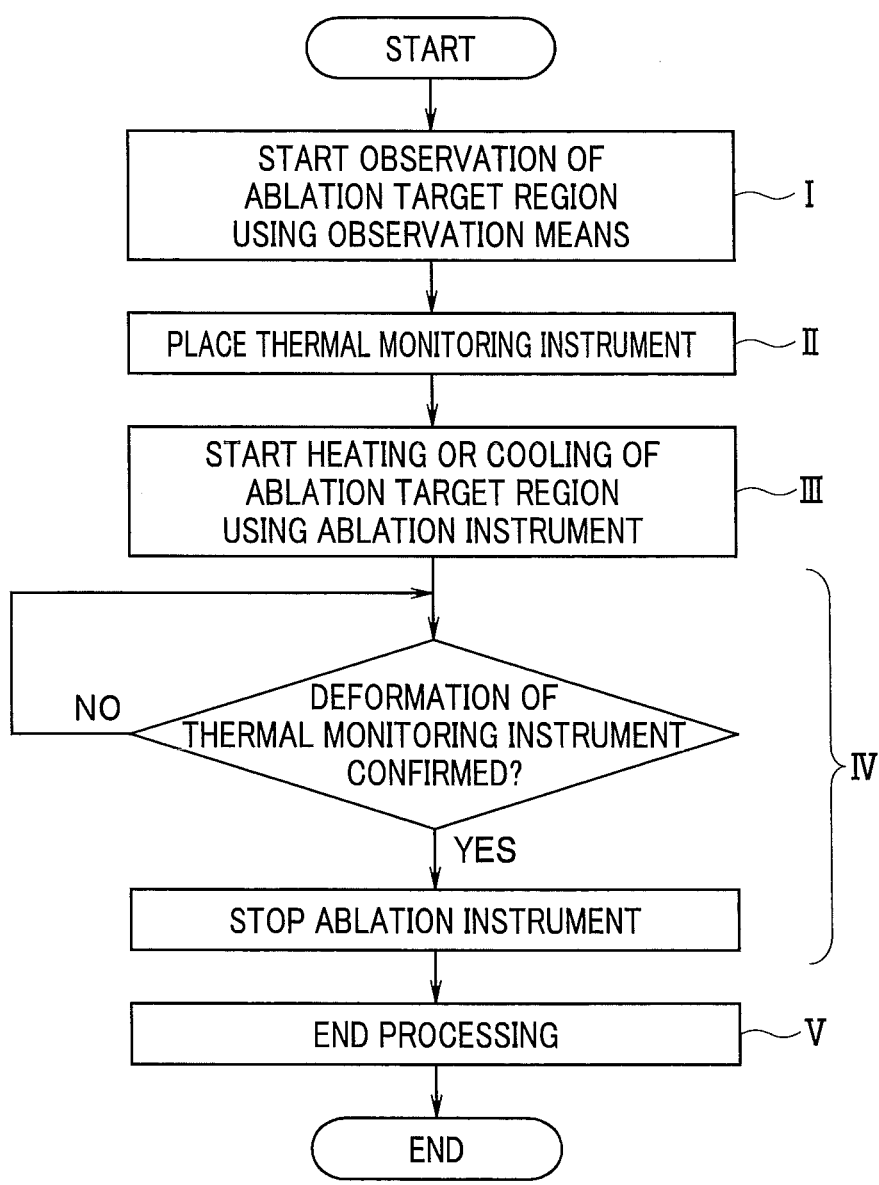
FIG. 4 is a flowchart of ablation.

Next, an ablation method according to the present embodiment will be described. FIG. 4 is a flowchart of the ablation method.

Figure 5:
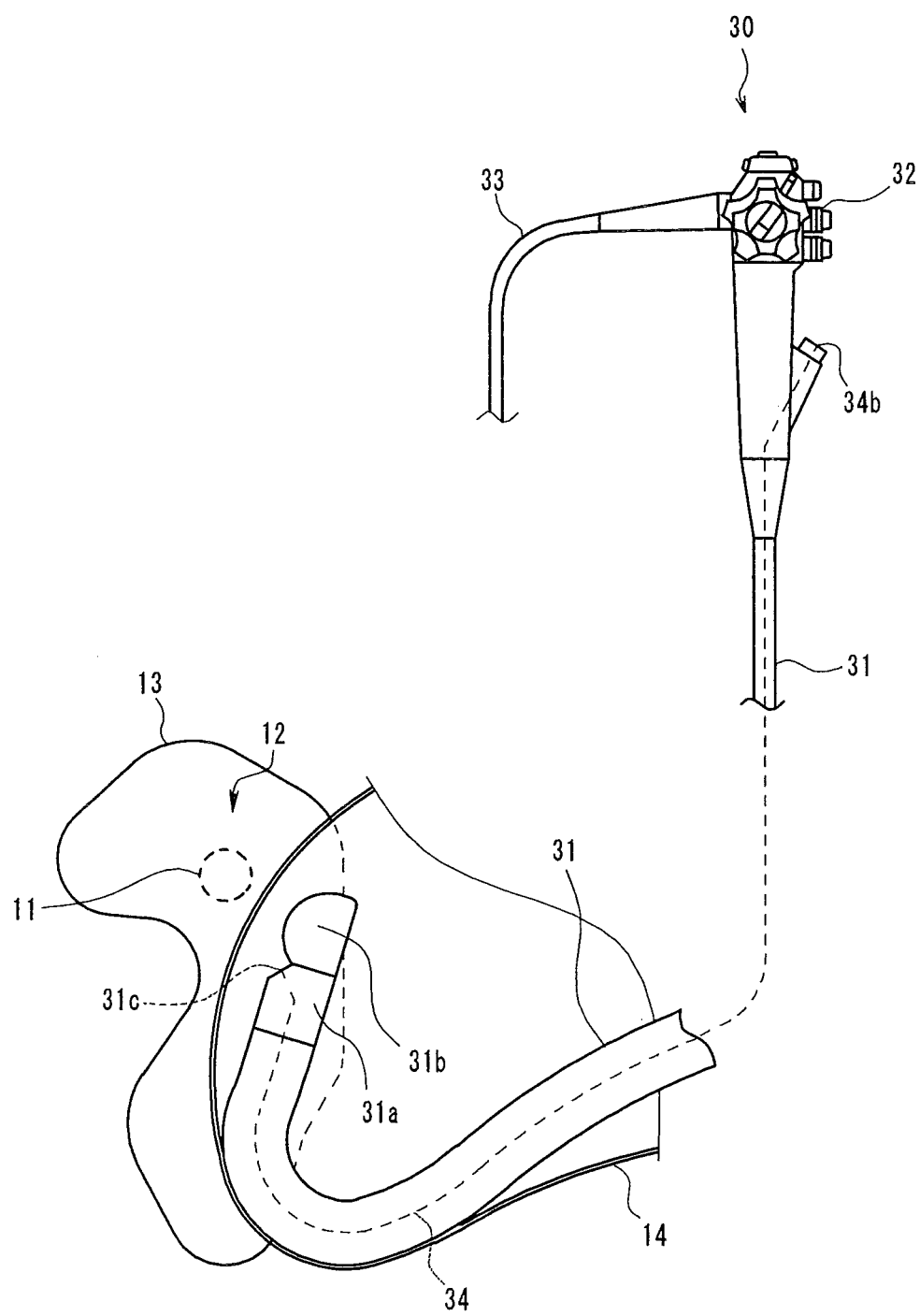
FIG. 5 is a diagram illustrating a step I.

In the ablation method, first, a step I of starting observation of a target region 11 and the periphery of the target region 11 using observation means is performed. In the present embodiment, a human body, which is a subject, is placed, for example, in left lateral decubitus position, and as illustrated in FIG. 5, an ultrasound endoscope 30, which is the observation means, is inserted into a stomach 14, which is a digestive tract. Then, tissues in the target region 11 and the periphery thereof inside a pancreas 13 are observed using an ultrasound tomographic image of the pancreas 13 obtained by the ultrasound endoscope 30. Since a configuration of the ultrasound endoscope 30 and a method of observation using the ultrasound endoscope 30 are known, a detailed description thereof will be omitted.

The ultrasound endoscope 30 roughly includes an insertion portion 31 that can be introduced into a subject, and an operation portion 32 positioned at a proximal end of the insertion portion 31. In a distal end portion 31a of the insertion portion 31, e.g., an ultrasound transducer 31b that transmits/receives ultrasound, a non-illustrated image pickup apparatus and a non-illustrated illumination apparatus for picking up an optical image, and a distal end-side opening portion 31c of a treatment instrument channel 34 are provided. An ultrasound tomographic image that can be obtained by driving the ultrasound transducer 31b, and an optical image that can be obtained by driving the image pickup apparatus are displayed on a non-illustrated image display apparatus connected to an operation portion 32 via a universal cord 33 extending from the operation portion 32. A surgeon can observe the target region 11 and the periphery of the target region 11 on the ultrasound tomographic image displayed on the image display apparatus.

Note that depending the position of the target region 11, the target region 11 may be observed using an ultrasound observation apparatus, which is observation means, placed on a body surface of the subject. Also, the observation means may be an apparatus that obtains a tomographic image of a subject using X rays.

Figure 6:
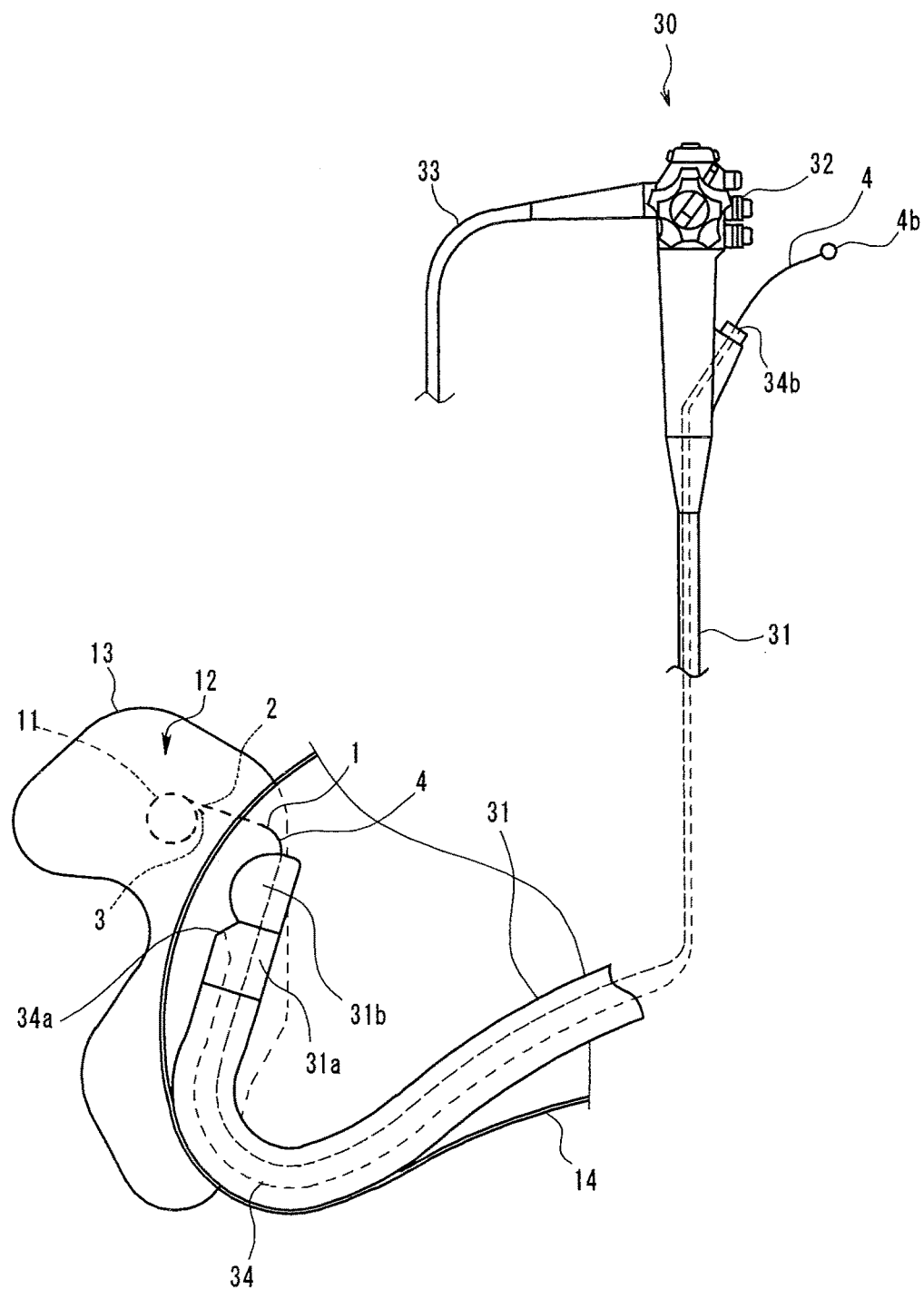
FIG. 6 is a diagram illustrating a step II.
Figure 7:
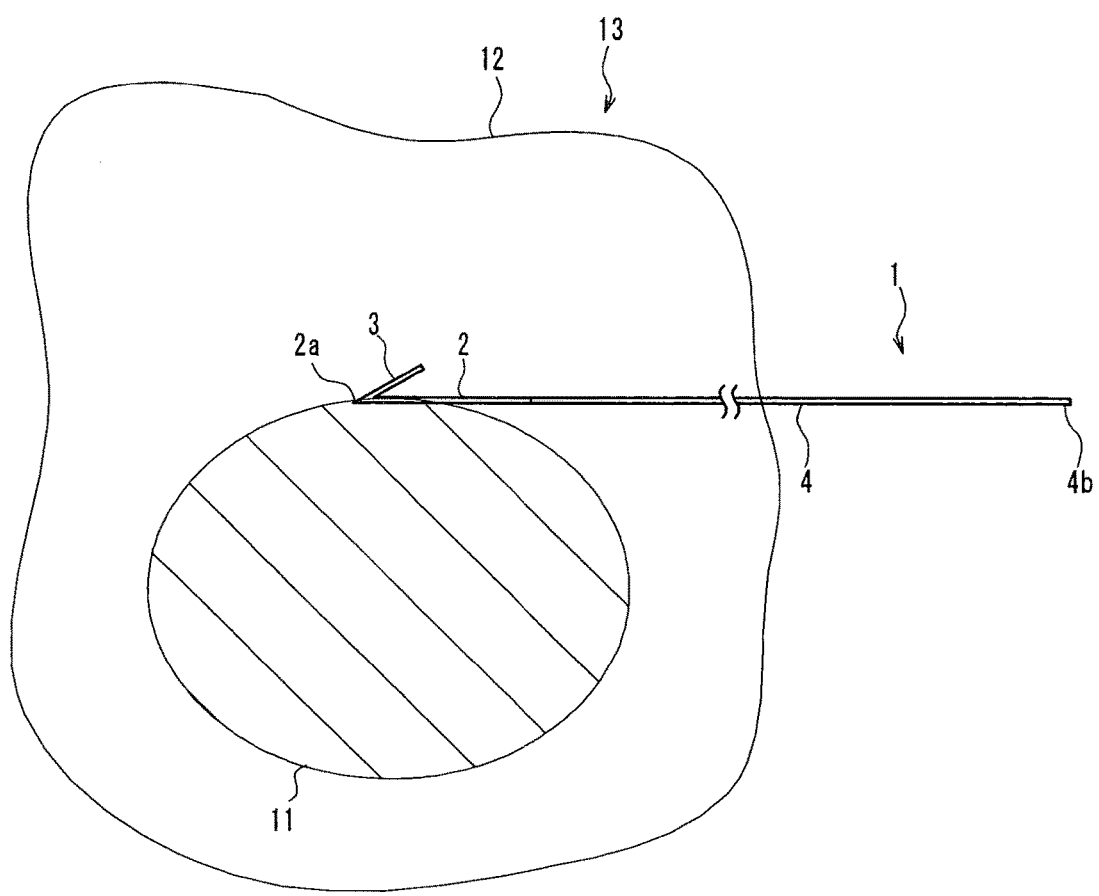
FIG. 7 is a diagram illustrating a position where the heat monitoring instrument is placed relative to an ablation target region and a conservation region in the step II.

In a next step II, under observation via the ultrasound endoscope 30, which is the observation means, as illustrated in FIGS. 6 and 7, the insertion portion 2 of the heat monitoring instrument 1 is inserted into a boundary between the target region 11 and a conservation region 12.

Here, in the present embodiment, the target region 11 is a region in which a tissue to be heated to a temperature exceeding the predetermined temperature Th by operation of the ablation instrument 20 exists. In the present embodiment, as described above, the target region 11 includes all or a part of tumor cells existing in the pancreas 13. If an object of the ablation is to kill all the tumor cells, the target region 11 includes all the tumor cells. Also, if an object of the ablation is to kill a part of the tumor cells for tumor cell reduction, the target region 11 includes, for example, only a part of the collection of tumor cells. In other words, if an object of the ablation is to kill the tumor cells, an outer edge of the collection of tumor cells and an outer edge of the target region 11 do not necessarily correspond to each other.

The conservation region 12 is a region including a tissue surrounding the target region 11, and thus is a region in which a tissue that should not be heated to a temperature exceeding the predetermined temperature Th by operation of the ablation instrument 20 exists. In other words, the conservation region 12 is a region that is adjacent to the target region and includes a tissue that should not be ablated.

In the present embodiment illustrated, the insertion portion 2 of the heat monitoring instrument 1 is introduced into the body of the subject via a duct included in the ultrasound endoscope 30, and under observation via the ultrasound endoscope 30, the insertion portion 2 is put into a pancreas 13 from the inside of a stomach 14 and then the distal end portion 2a of the insertion portion 2 is brought to the boundary between the target region 11 and the conservation region 12. In this case, the proximal end portion 4b of the linear member 4 of the heat monitoring instrument 1 extends to the outside of the body of the subject.

Note that the duct included in the ultrasound endoscope 30, through which the heat monitoring instrument 1 is inserted, may be the treatment instrument channel 34 or may also be a duct provided in the ultrasound endoscope 30 separately from the treatment instrument channel 34. Also, a duct through which the linear member 4 is inserted may be a cylindrical member inserted inside the subject separately from the ultrasound endoscope 30.

Note that a path on which the insertion portion 2 of the heat monitoring instrument 1 is brought to the boundary between the target region 11 and the conservation region 12 is not limited to that in the present embodiment and is arbitrarily determined according to the position of the target region 11. The insertion portion 2 of the heat monitoring instrument 1 may be brought to the boundary between the target region 11 and the conservation region 12, for example, via a path that passes from a body surface of the subject to the inside of the body of the subject via the skin.

Also, in the step II, a plurality of heat monitoring instruments 1 to be inserted into the boundary between the target region 11 and the conservation region 12 may be provided. If a plurality of heat monitoring instruments 1 are used, it is preferable to place the plurality of heat monitoring instruments 1 so as to surround the target region 11.

Figure 8:
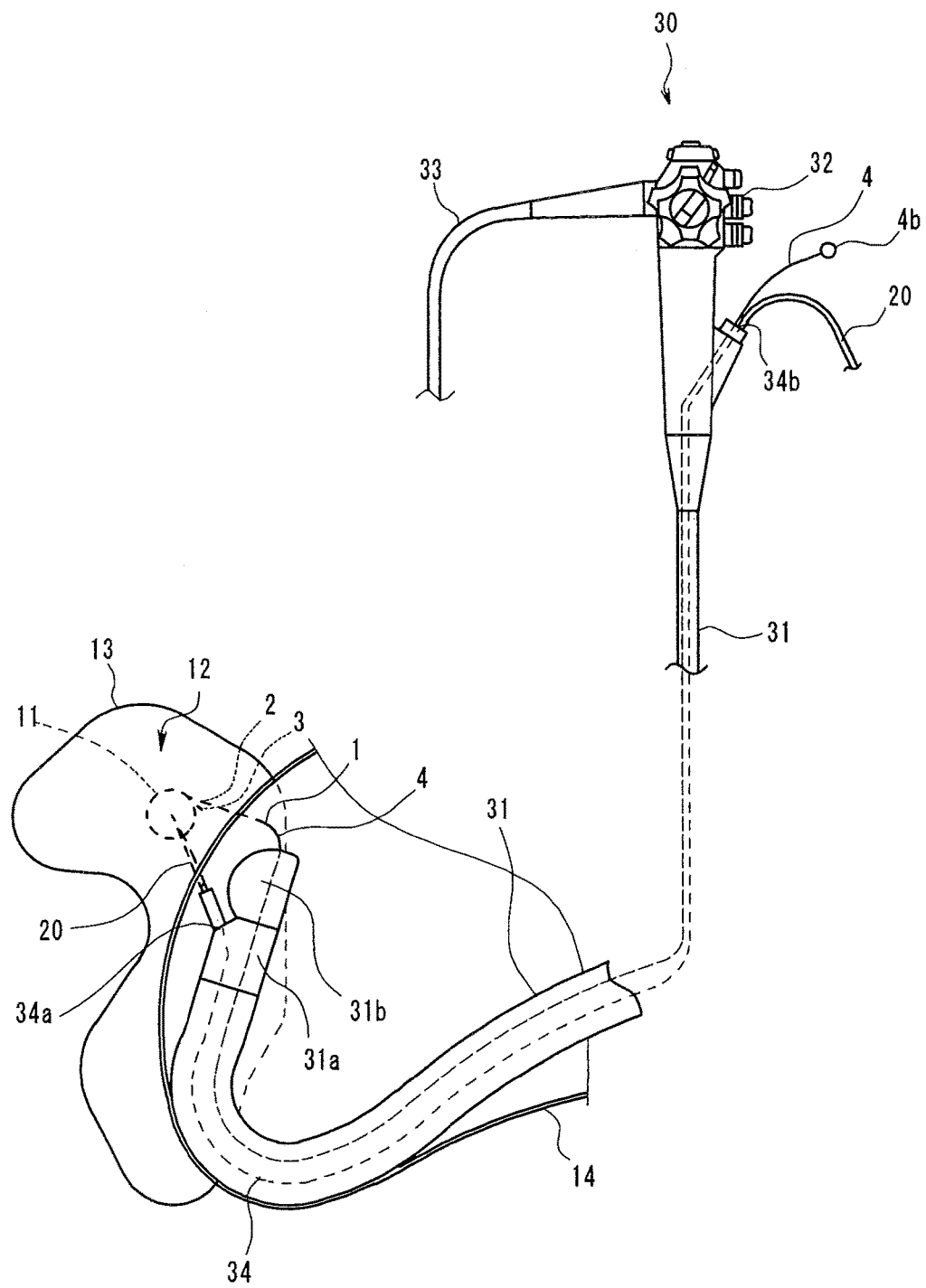
FIG. 8 is a diagram illustrating a step III.
Figure 9:
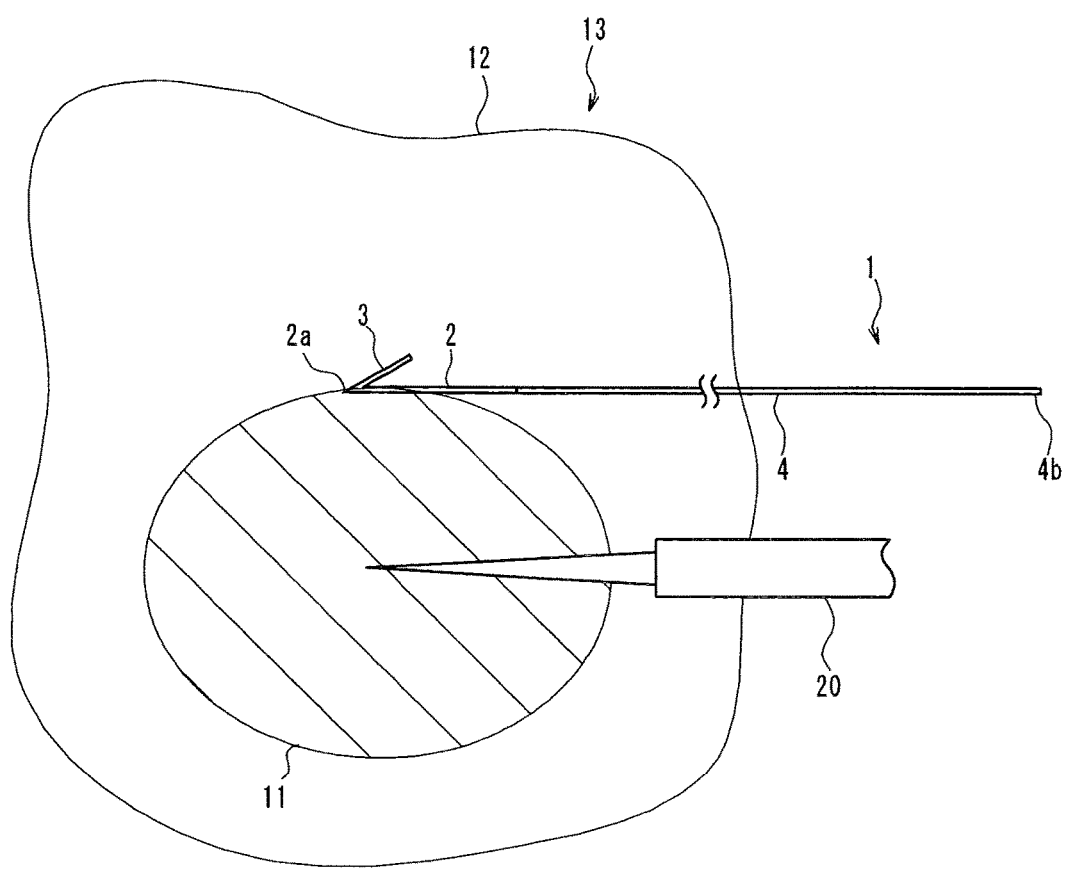
FIG. 9 is an enlarged view of the target region in the step III.

In a next step III, under observation via the ultrasound endoscope 30, which is the observation means, as illustrated in FIGS. 8 and 9, the ablation instrument 20 is placed on the ablation target region 11 and heating or cooling of the target region 11 is started by making the ablation instrument 20 operate.

As described above, in the present embodiment, as an example, the ablation instrument 20 is an apparatus that makes a tissue generate heat by means of application of a high-frequency voltage such as microwave or radio wave or ultrasound irradiation. In the present embodiment illustrated, the ablation instrument 20 is introduced into the body of the subject via the treatment instrument channel 34 included in the ultrasound endoscope 30, and under observation via the ultrasound endoscope 30, the insertion portion 2 is put into the target region 11 of the pancreas 13 from the inside of the stomach 14. Then, heating of the target region 11 is started by making the ablation instrument 20 operate.

Note that a path on which the ablation instrument 20 is brought to the target region 11 is not limited to a duct included in the ultrasound endoscope 30. For example, the ablation instrument 20 may be brought to the target region 11 via a cylindrical member inserted inside the subject separately from the ultrasound endoscope 30. Also, for example, the ablation instrument 20 may be brought to the target region 11 via a path that passes from a body surface of the subject to the inside of the body of the subject via the skin.

In a next step IV, while heating or cooling using the ablation instrument 20 is performed, whether or not the heat monitoring instrument 1 deforms is checked, and if deformation of the heat monitoring instrument 1 is confirmed, the heating or the cooling using the ablation instrument 20 is stopped.

A method for confirming deformation of the heat monitoring instrument 1 is not specifically limited. In the present embodiment, as described above, the insertion portion 2 of the heat monitoring instrument 1 is inserted into a tissue and then change in a tensile force that can be applied to the linear member 4 is observed, enabling checking whether or not deformation of the insertion portion 2 occurs. Therefore, in the step IV in the present embodiment, as an example, a surgeon or an assistant for the surgeon pulls the proximal end portion 4b of the linear member 4 to continuously or intermittently apply a tensile force to the linear member 4. Then, it is determined that the insertion portion 2 deforms, at the point of time when the tensile force that can be applied to the linear member 4 decreases.

Figure 10:
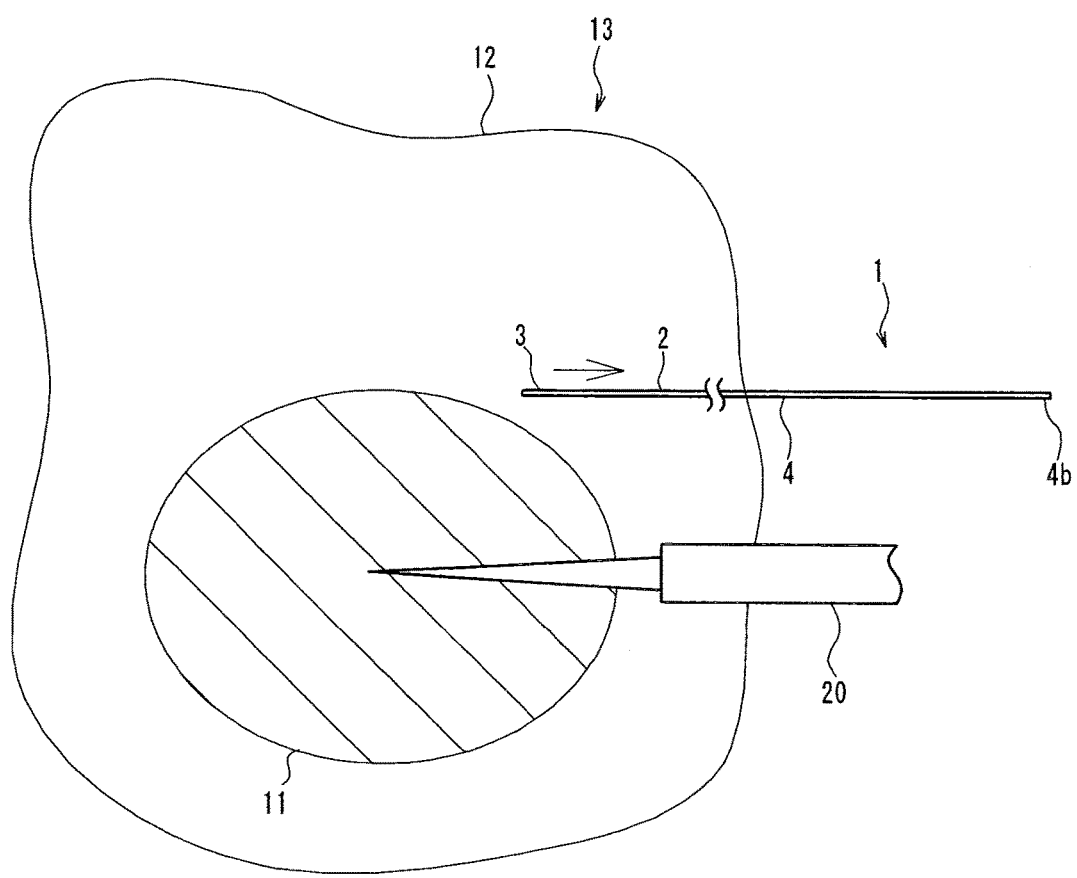
FIG. 10 is a diagram for describing a step IV.

Note that the point of time when the tensile force that can be applied to the linear member 4 decreases is a point of time when the insertion portion 2 deforms and thereby the tissue and the locking portion 3 are disengaged, as illustrated in FIG. 10, and thus can be regarded as a point of time when the insertion portion 2 moves in a direction in which the insertion portion 2 is pulled out from the pancreas 13 and is thereby pulled out from the pancreas 13.

In the present embodiment, a case where the heat monitoring instrument 1 deforms is a case where the temperature of the insertion portion 2 exceeds the predetermined temperature Th. Therefore, at the point of time when deformation of the heat monitoring instrument 1 is confirmed, the surgeon can see that the boundary between the target region 11 and the conservation region 12 on which the insertion portion 2 is placed is heated to the predetermined temperature Th.

As described above, in the present embodiment, change in temperature of the target region 11 and the peripheral conservation region 12 resulting from operation of the ablation instrument 20 can be perceived using the heat monitoring instrument 1. Then, operation of the ablation instrument 20 is stopped at a stage where deformation of the heat monitoring instrument 1 is confirmed, enabling prevention of the region heated to a temperature exceeding the predetermined temperature Th from extending to the conservation region 12 surrounding the target region 11.

In the step IV, monitoring change in tensile force that can be applied to the linear member 4 eliminates the need to continuously monitor the state of the insertion portion 2 existing in the tissue via an ultrasound tomographic image in order to check whether or not deformation of the insertion portion 2 occurs. Thus, even if the insertion portion 2 is placed outside the ultrasound tomographic image from the ultrasound endoscope 30, whether or not deformation of the insertion portion 2 occurs can be checked. Accordingly, irrespective of a range of an ultrasound tomographic image picked up by the ultrasound endoscope 30 during operation of the ablation instrument 20, the heat monitoring instrument 1 can be placed at an arbitrary position.

In a next step V, end processing of removing the heat monitoring instrument 1 and the ablation instrument 20 from the inside of the subject is performed. In the present embodiment, the ultrasound endoscope 30 is also removed from the inside of the subject. Also, in the end processing, e.g., saturation is performed as necessary.

As described above, in the present embodiment, a surgeon can easily and reliably check change in temperature of a tissue at a desired position when ablation is performed, using the heat monitoring instrument 1. In particular, in the present embodiment, whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Also, the heat monitoring instrument 1 has a simple structure in which a locking portion 3 is provided in an insertion portion 2 formed of a shape-memory alloy and a linear member 4 is coupled to the insertion portion 2 and is thus inexpensive, enabling reduction of costs for ablation.

Second Embodiment

A second embodiment of the present invention will be described below. The below description is provided only in terms of differences from the first embodiment, components that are similar to those of the first embodiment are provided with reference numerals that are the same as those of the first embodiment and description thereof will arbitrarily be omitted.

The present embodiment is different from the first embodiment in that a target region 11 is cooled using an ablation instrument 20. A heat monitoring instrument 1 used for ablation according to the present embodiment includes an insertion portion 2 formed of a shape-memory alloy that deforms when the shape-memory alloy is cooled from a temperature that is equal to or exceeding a predetermined temperature Tl to a temperature that is below the predetermined temperature Tl.

Figure 11:
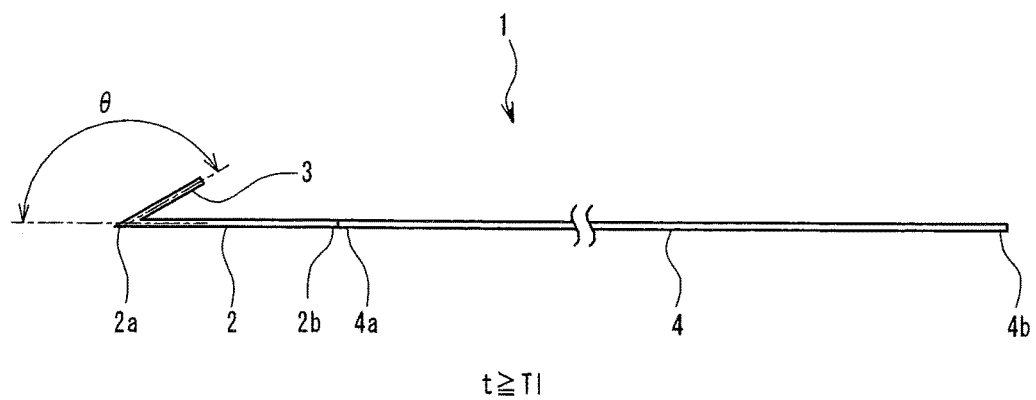
FIG. 11 is a diagram illustrating a configuration of a heat monitoring instrument according to a second embodiment.
Figure 12:
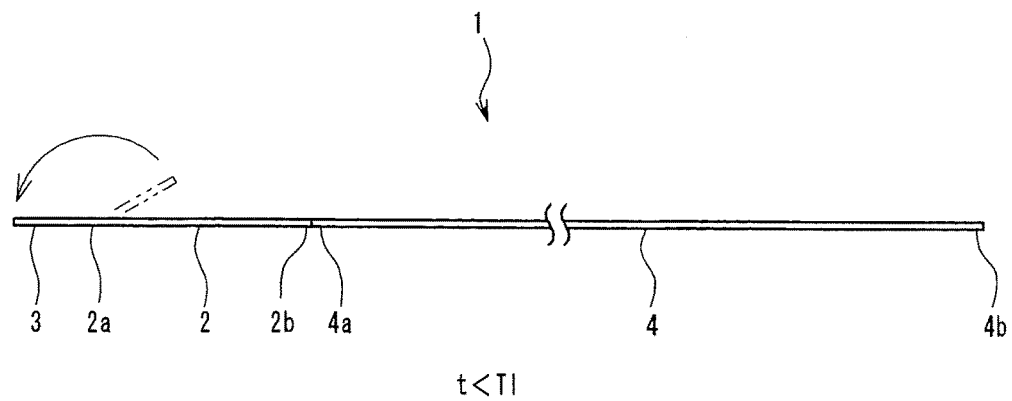
FIG. 12 is a diagram illustrating a state in which an insertion portion of the heat monitoring instrument according to the second embodiment deforms.

FIG. 11 illustrates a case where a temperature t of the insertion portion 2 is equal to or exceeds the predetermined temperature Tl. FIG. 12 illustrates a case where the temperature t of the insertion portion is below the predetermined temperature Tl.

As illustrated in FIG. 11, when the temperature t of the insertion portion 2 is equal to or exceeds the predetermined temperature Tl, the locking portion 3 has a hook-like shape. When the insertion portion 2 is inserted inside a tissue of a living object such as a human body, which is a subject, and the temperature of the insertion portion 2 is equal to or exceeds the predetermined temperature Tl, the hook-like locking portion 3 engages with a surrounding tissue.

As illustrated in FIG. 12, when the temperature t of the insertion portion 2 is below the predetermined temperature Tl, the insertion portion 2 deforms into a linear shape. When the insertion portion 2 is inserted inside a tissue of a living body such a human body, which is a subject, and the temperature of the insertion portion 2 is below the predetermined temperature Tl, the insertion portion 2 deforms and the locking portion 3 and the surrounding tissue are disengaged.

The ablation instrument 20 according to the present embodiment includes a needle tube for injecting a low-temperature liquid such as liquid nitrogen into the target region 11. The ablation instrument 20 injects liquid nitrogen into the target region 11 with a distal end of the needle tube inserted in the target region 11 to cool the target region 11.

A process of an ablation method is as in the flowchart illustrated in FIG. 4, and is similar to that of the first embodiment.

In other words, in the ablation method, first, in a step I, observation of an ablation target region 11 and the periphery of the target region 11 is started using observation means. In a next step II, under observation via the observation means, the insertion portion 2 of the heat monitoring instrument 1 is inserted into a boundary between the ablation target region 11 and a conservation region 12.

In a next step III, under observation via the observation means, the ablation instrument 20 is placed on the ablation target region 11 and cooling of the target region 11 is started by making the ablation instrument 20 operate. Then, in a next step IV, while the cooling using the ablation instrument 20 is performed, whether or not the heat monitoring instrument 1 deforms is checked, and if deformation of the heat monitoring instrument 1 is confirmed, the cooling using the ablation instrument 20 is stopped.

In the present embodiment, also, as in the first embodiment, a surgeon can easily and reliably check change in temperature of a tissue at a desired position when ablation is performed, using the heat monitoring instrument 1. Also, since whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Also, the heat monitoring instrument 1 has a simple structure in which a locking portion 3 is provided in an insertion portion 2 formed of a shape-memory alloy and a linear member 4 is coupled to the insertion portion 2 and is thus inexpensive, enabling reduction of costs for ablation.

Third Embodiment

A third embodiment of the present invention will be described below. The below description is provided only in terms of differences from the first embodiment, components that are similar to those of the first embodiment are provided with reference numerals that are the same as those of the first embodiment and description thereof will arbitrarily be omitted.

Figure 13:
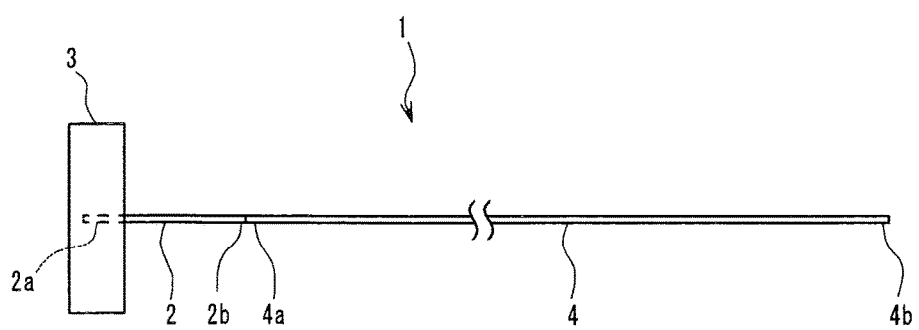
FIG. 13 is a diagram illustrating a configuration of a heat monitoring instrument according to a third embodiment.

The present embodiment is different from the first embodiment in terms of a configuration of a heat monitoring instrument 1. The heat monitoring instrument 1 according to the present embodiment, which is illustrated in FIG. 13, includes a locking portion 3 that melts or softens and thereby deforms when a temperature thereof exceeds a predetermined temperature Th, in a distal end portion 2a of an insertion portion 2 formed of a linear member such as a string or a metal wire. A material included in the locking portion 3 is, for example, bees wax, bone wax or paraffin.

The locking portion 3 has, for example, a T-shape as illustrated in the figure when the temperature of the locking portion 3 is equal to or below the predetermined temperature Th. When the locking portion 3 is inserted inside a tissue and the temperature of the locking portion 3 is equal to or below the predetermined temperature Th, the locking portion 3 engages with the tissue like an anchor.

In the present embodiment, in a step IV, if the temperature of the locking portion 3 exceeds the predetermined temperature Th, the locking portion 3 deforms according to a tensile force applied to a linear member 4, whereby the locking portion 3 and the tissue are disengaged. Accordingly, as in the first embodiment, whether or not deformation of the insertion portion 2 occurs can be checked by monitoring change in the tensile force that can be applied to the linear member 4.

In the present embodiment, also, as in the first embodiment, a surgeon can easily and reliably check change in temperature of a tissue at a desired position when ablation is performed, using the heat monitoring instrument 1. Also, since whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Also, the heat monitoring instrument 1 has a simple structure in which a locking portion 3 formed of, e.g., bees wax is provided in an insertion portion 2 formed of, e.g., a string or a metal wire and is thus inexpensive, enabling reduction of costs for ablation.

Fourth Embodiment

A fourth embodiment of the present invention will be described below. The below description is provided only in terms of differences from the first, second and third embodiments, and components that are similar to those of the first, second and third embodiments are provided with reference numerals that are the same as those of the first, second and third embodiments and description thereof will arbitrarily be omitted.

The present embodiment is different from the first embodiment in terms of a configuration of a heat monitoring instrument 1. In the above-described first, second and third embodiments, in a state in which the insertion portion 2 of the heat monitoring instrument 1 is inserted inside a tissue of a subject, the locking portion 3 directly engages with the tissue. On the other hand, in the present embodiment, an insertion portion 2 of the heat monitoring instrument 1 is housed in a cylindrical member 5 and a locking portion 3 engages with the cylindrical member 5.

Figure 14:
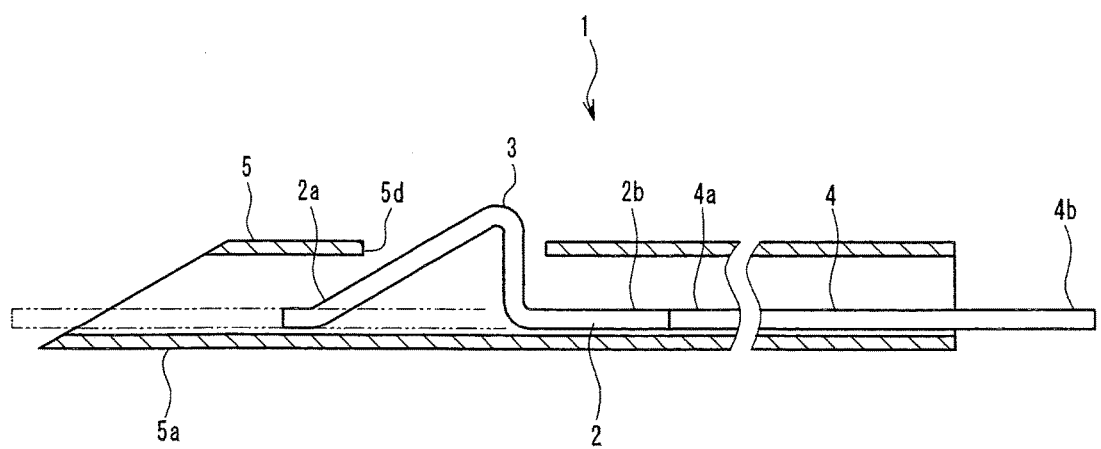
FIG. 14 is a diagram illustrating a configuration of a heat monitoring instrument according to a fourth embodiment.

As illustrated in FIG. 14, the heat monitoring instrument 1 according to the present embodiment includes the cylindrical member 5, the insertion portion 2 inserted in the cylindrical member 5, and a linear member 4. In a distal end portion 2a of the insertion portion 2, the locking portion 3 is provided.

In the present embodiment, as an example, the cylindrical member 5 is a needle tube that can be inserted into a tissue of a subject. In a wall surface in the vicinity of a distal end portion 5a of the cylindrical member 5, a through hole 5d is provided. The linear member 4 is an elongated linear member as in the above-described embodiments.

The insertion portion 2 is formed of a linear shape-memory alloy. In the distal end portion 2a, which is one end of the insertion portion 2, the locking portion 3 is provided. Also, a proximal end portion 2b, which is the other end of the insertion portion 2, is coupled to a distal end portion 4a of the linear member 4.

The insertion portion 2 of the present embodiment deforms into a linear shape if a temperature of the insertion portion 2 exceeds a predetermined temperature Th. The locking portion 3 is formed by folding the distal end portion 2a of the linear insertion portion 2 into a hook-like shape on a condition that the temperature of the locking portion 3 is equal to or below the predetermined temperature. The locking portion 3 projects to the outside of the cylindrical member 5 through the through hole 5d formed in the wall surface of the cylindrical member 5. Therefore, when the temperature of the locking portion 3 is equal to or below the predetermined temperature Th, the locking portion 3 engages with the cylindrical member 5. If the temperature of the locking portion 3 exceeds the predetermined temperature Th, as indicated by the alternate long and two short dashes line in FIG. 14, the locking portion deforms into a linear shape and disengages from the cylindrical member 5.

Also, in a state in which the locking portion 3 engages with the through hole 5d of the cylindrical member 5, a proximal end portion 4b of the linear member 4 extends from a proximal end of the cylindrical member 5 to the outside.

In an ablation method according to the present embodiment, in a step II, the distal end portion 5a of the cylindrical member 5 of the heat monitoring instrument 1 is inserted into a boundary between a target region 11 and a conservation region 12.

Then, in a step IV, the proximal end portion 4b of the linear member 4 is pulled with the cylindrical member 5 fixed, and change in a tensile force that can be applied to the linear member 4 is monitored, enabling checking whether or not deformation of the insertion portion 2 occurs.

Note that if the ablation is of the type that cools a target region 11 as in the second embodiment, the locking portion 3 according to present embodiment has a hook-like shape and engages with the through hole 5d when the temperature t is equal to or exceeds a predetermined temperature Tl, and deforms into a linear shape and thereby disengages from the through hole 5d when the temperature is below the predetermined temperature Tl.

Also, as in the third embodiment, the locking portion 3 may be of a type that is formed of a material that melts or softens and thereby deforms when a temperature of the material exceeds the predetermined temperature Th and deforms so as to disengage from the through hole 5d when the temperature of the locking portion exceeds the predetermined temperature Th.

In the present embodiment, also, as in the first, second and third embodiments, a surgeon can easily and reliably check change in temperature of a tissue at a desired position when ablation is performed, using the heat monitoring instrument 1. Also, since whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Furthermore, the heat monitoring instrument 1 has a simple structure and is thus inexpensive, enabling reduction of costs for ablation.

Fifth Embodiment

A fifth embodiment of the present invention will be described below. The below description is provided only in terms of differences from the first to fourth embodiments, and components that are similar to those of the first to fourth embodiments are provided with reference numerals that are the same as those of the first to fourth embodiments and description thereof will arbitrarily be omitted.

The present embodiment is different in that monitoring a tensile force that can be applied to a linear member 4 of a heat monitoring instrument 1 in a step IV is performed using a traction apparatus 40.

Figure 15:
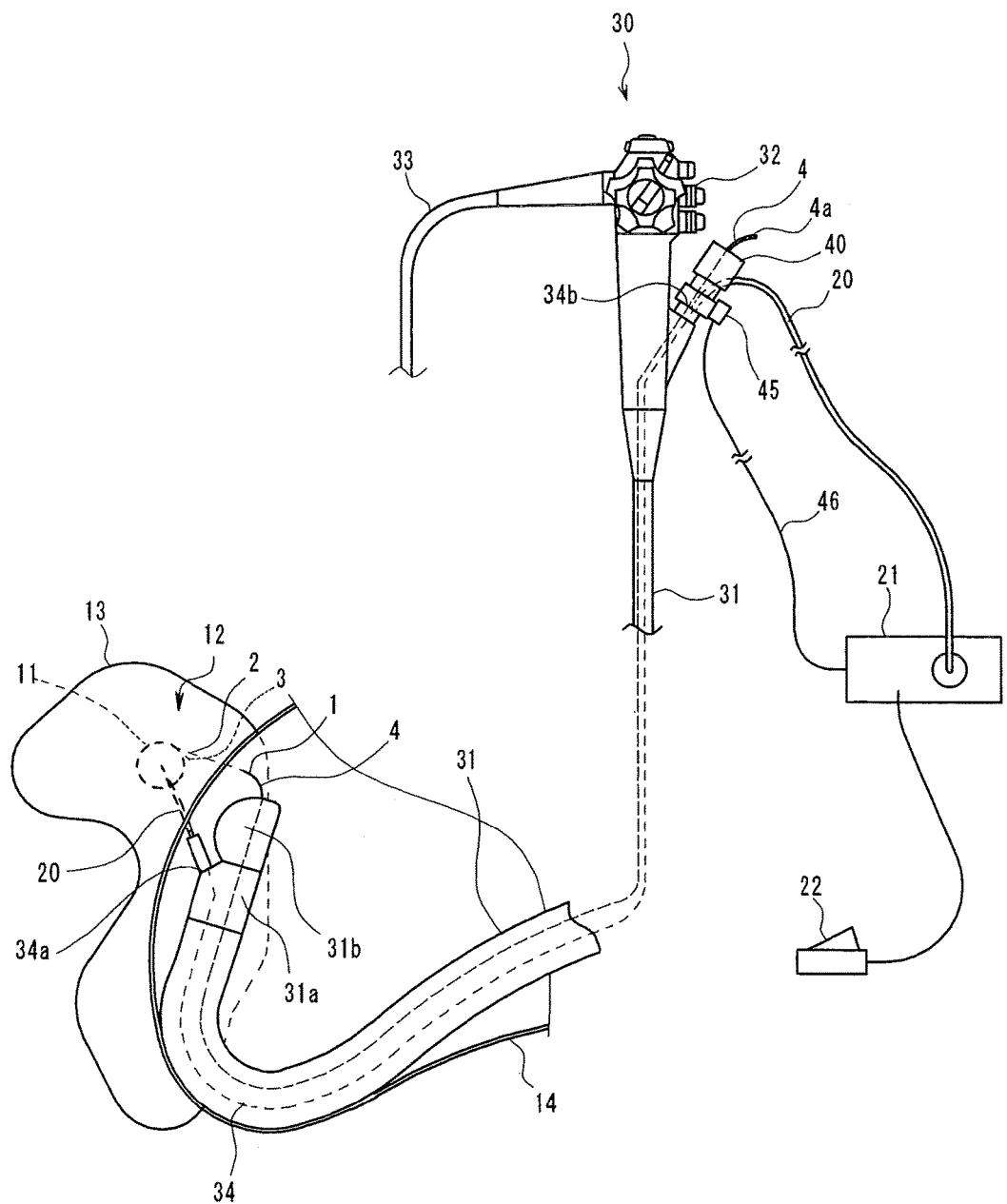
FIG. 15 is a diagram illustrating an ablation method according to a fifth embodiment.
Figure 16:
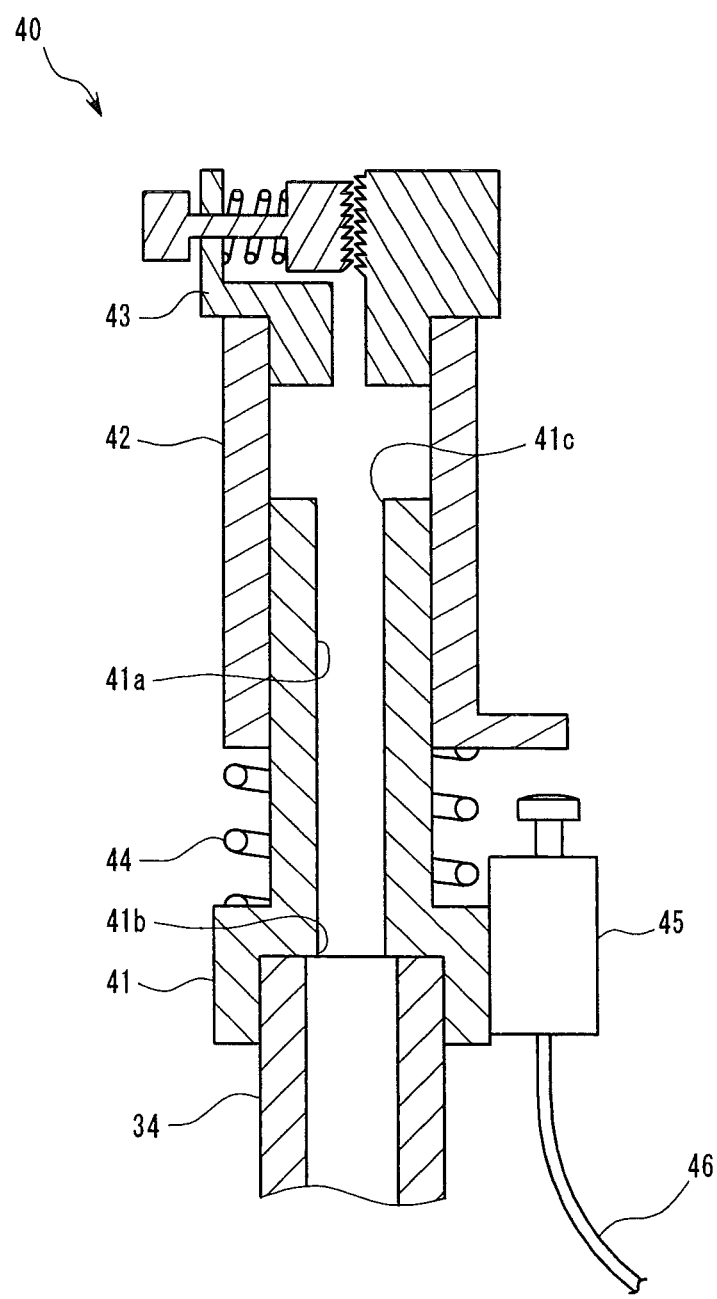
FIG. 16 is a cross-sectional view of a traction apparatus according to the fifth embodiment.

As illustrated in FIG. 15, the traction apparatus 40 according to the present embodiment is fixed to a proximal end-side opening portion 34b of a treatment instrument channel 34 in an ultrasound endoscope 30. As illustrated in FIG. 16, the traction apparatus 40 includes a base portion 41, a slider 42, a holding portion 43, a biasing member 44 and a detection section 45.

The base portion 41 is a member fixed to the proximal end-side opening portion 34b. In the base portion 41, a through hole 41a is formed. In a state in which the base portion 41 is fixed to the proximal end-side opening portion 34b, one end 41b of the through hole 41a faces the proximal end-side opening portion 34b. Therefore, in a state in which the base portion 41 is fixed to the proximal end-side opening portion 34b, the through hole 41a and the treatment instrument channel 34 are connected.

The slider 42 is a member that moves relative to the base portion 41. The slider 42 moves relative to the base portion 41 along a center axis of the through hole 41a. The holding portion 43 is fixed to the slider 42.

The holding portion 43 is a member that moves relative to the base portion 41 along the center axis of the through hole 41a, together with the slider 42. The holding portion 43 is disposed facing the other end 41c of the through hole 41a provided in the base portion 41. In other words, the holding portion 43 advances/retracts along the center axis of the through hole 41a in such a manner a distance between the holding portion 43 and the other end 41c of the through hole 41a changes.

The holding portion 43 is configured to hold a proximal end portion 4b of the linear member 4. The holding of the proximal end portion 4b of the linear member 4 by the holding portion 43 can be cancelled by a user. In the present embodiment illustrated, as an example, the holding portion 43 is configured to pinch the proximal end portion 4b of the linear member 4 from the sides like a clip.

The biasing member 44 is a member formed of, e.g., a spring that biases the slider 42 in a direction away from the proximal end-side opening portion 34b. In other words, the biasing member 44 biases the holding portion 43 in a direction away from the other end 41c of the through hole 41a along the center axis of the through hole 41a.

Figure 17:
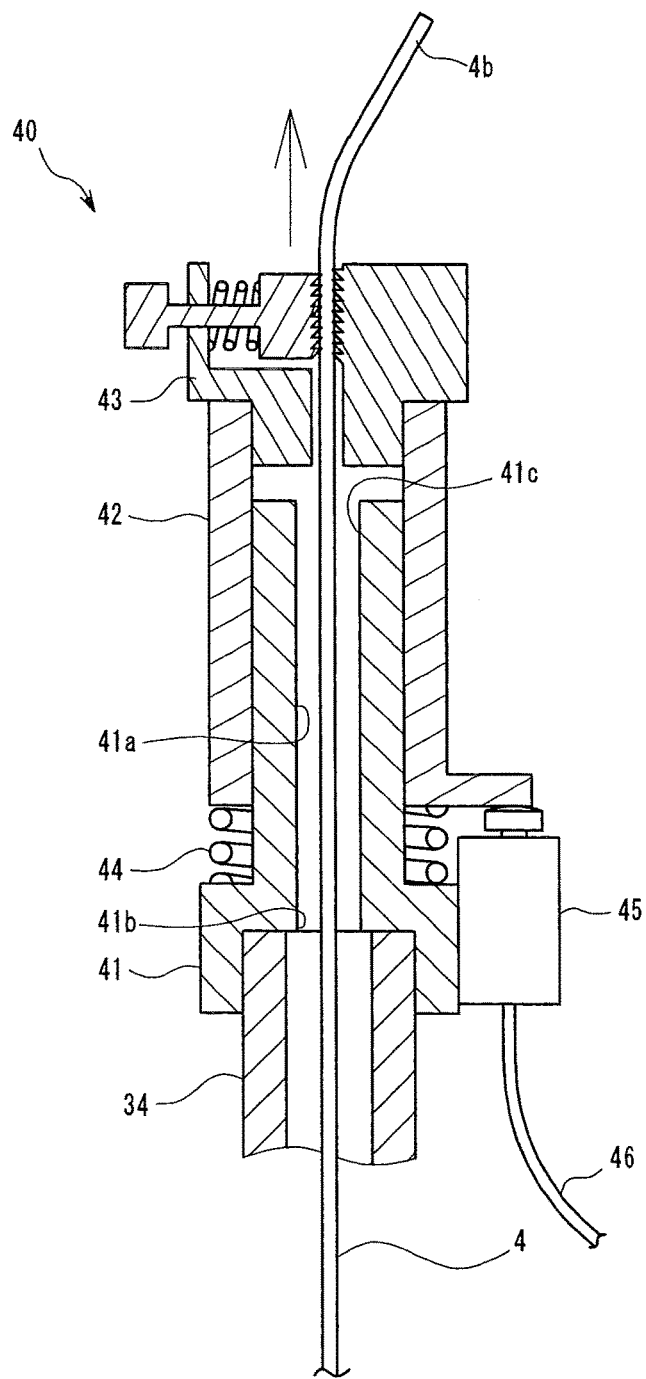
FIG. 17 is a diagram illustrating a state in which a proximal end portion of a linear member is pulled by means of the traction apparatus according to the fifth embodiment.

In a step II, an insertion portion 2 of the heat monitoring instrument 1 is inserted into a boundary between a target region 11 and a conservation region 12, and then, as illustrated in FIG. 17, in a state in which the holding portion 43 is brought close to the other end 41c of the through hole 41a against a biasing force of the biasing member 44, the proximal end portion 4b of the linear member 4 extending out from the proximal end-side opening portion 34b is held by the holding portion 43. Consequently, the biasing force of the biasing member 44 is transmitted to the linear member 4, whereby a tensile force is applied to the linear member 4.

The detection section 45 detects loss of the tensile force applied to the linear member 4 by the traction apparatus 40. The detection section 45 is electrically connected to a drive apparatus 21 for an ablation instrument 20 via an electric cable 46.

The drive apparatus 21 can make the ablation instrument 20 operate, for example, during a period of time in which a foot switch 22 is kept on by a user. Also, if loss of the tensile force applied to the linear member 4 is detected by the detection section 45 during operation of the ablation instrument 20, the drive apparatus 21 stops the ablation instrument 20.

Although a configuration of the detection section 45 is not specifically limited, as illustrated in FIGS. 16 and 17, in the present embodiment, as an example, the detection section 45 is configured as a push switch that is turned on/off according to advancement/retraction of the slider 42 and the holding portion 43.

The detection section 45, which is a push switch, is fixed to the base portion 41. As illustrated in FIG. 17, in a state in which the slider 42 and the holding portion 43 are brought close to the other end 41c of the through hole 41a, the detection section 45 is in contact with the slider 42 and thus in an on state. In other words, in a state in which a tensile force is applied to the linear member 4, the detection section 45 is in an on state.

On the other hand, in a state in which no tensile force is applied to the linear member 4, that is, the slider 42 and the holding portion 43 are located at a position away from the other end 41c of the through hole 41a by the biasing force of the biasing member 44, the detection section 45 is spaced from the slider 42 and thus in an off state.

In an ablation method using the traction apparatus 40 and the drive apparatus 21 configured as described above, in a step IV, checking of whether or not deformation of the insertion portion 2 occurs and stoppage of the ablation instrument 20 can automatically be performed, enabling reduction in burden on the surgeon.

Note that the traction apparatus 40 may be configured to apply a tensile force to the linear member 4 of the heat monitoring instrument 1 by means of another method such as an electric motor.

In the present embodiment, also, as in the first to fourth embodiments, a surgeon can easily and reliably check change in temperature of a tissue at a desired position when ablation is performed, using the heat monitoring instrument 1. Also, since whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Furthermore, the heat monitoring instrument 1 has a simple structure and is thus inexpensive, enabling reduction of costs for ablation.

Sixth Embodiment

A sixth embodiment of the present invention will be described below. The below description is provided only in terms of differences from the first, third, fourth and fifth embodiments, and components that are similar to those of the first, third, fourth and fifth embodiments are provided with reference numerals that are the same as those of the first, third, fourth and fifth embodiments and description thereof will arbitrarily be omitted.

In the above-described embodiments, whether or not deformation of the insertion portion 2 of the heat monitoring instrument 1 occurs is checked based on change in the tensile force applied to the linear member 4. On the other hand, in the present embodiment illustrated in FIGS. 18 and 19, whether or not deformation of an insertion portion 2 occurs is checked based on whether or not there is electrical conduction between a pair of electrodes 8b provided in the insertion portion 2.

Figure 18:
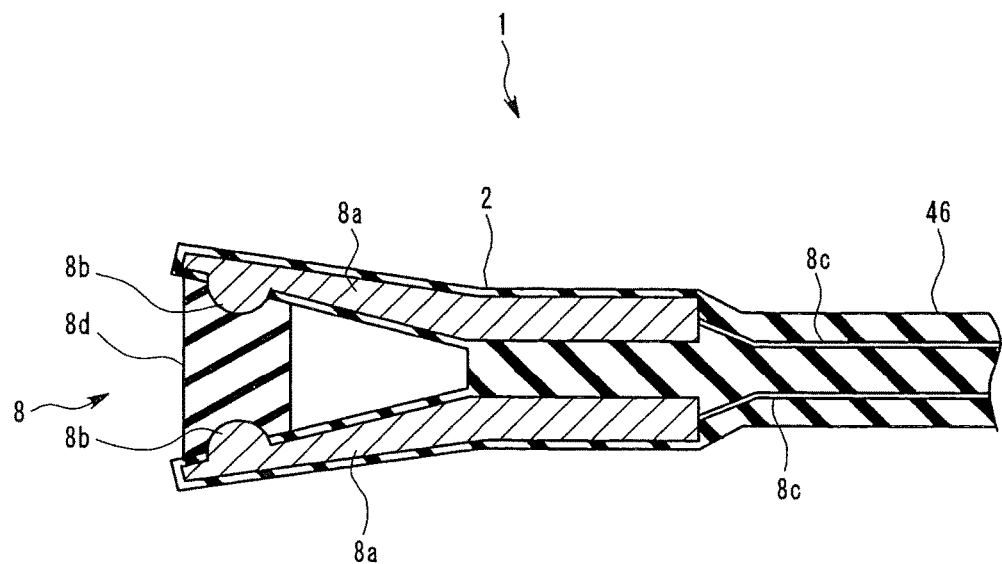
FIG. 18 is a diagram illustrating a configuration of a heat monitoring instrument according to a sixth embodiment.

As illustrated in FIG. 18, a heat monitoring instrument 1 according to the present embodiment includes a switch section 8 disposed in the insertion portion 2. The switch section 8 includes the pair of electrodes 8b, plate springs 8a and an insulating member 8d. The pair of electrodes 8b are disposed facing each other. The pair of electrodes 8b are biased in respective directions in which the pair of electrodes 8b are brought into contact with to each other by the plate springs 8a.

A conductive wire 8c extends out from each of the pair of electrodes 8b. The conductive wires 8c are electrically connected to a drive apparatus 21 of a non-illustrated ablation instrument 20 via an electric cable 46. The drive apparatus 21 stops the ablation instrument 20 if conduction between the pair of electrodes 8b is confirmed during operation of the ablation instrument 20.

Then, an insulating member 8d is held between the pair of electrodes 8b. The insulating member 8d is formed of a material that has an electrical insulation property and melts or softens when a temperature of the material exceeds a predetermined temperature Th. The material included in the insulating member 8d is, for example, bees wax, bone wax or paraffin.

When a temperature of the switch section 8 is equal to or below the predetermined temperature Th, as illustrated in FIG. 18, the pair of electrodes 8b are spaced from each other by the insulating member 8d interposed therebetween and thus there is no electrical conduction between the pair of electrodes 8b.

Figure 19:
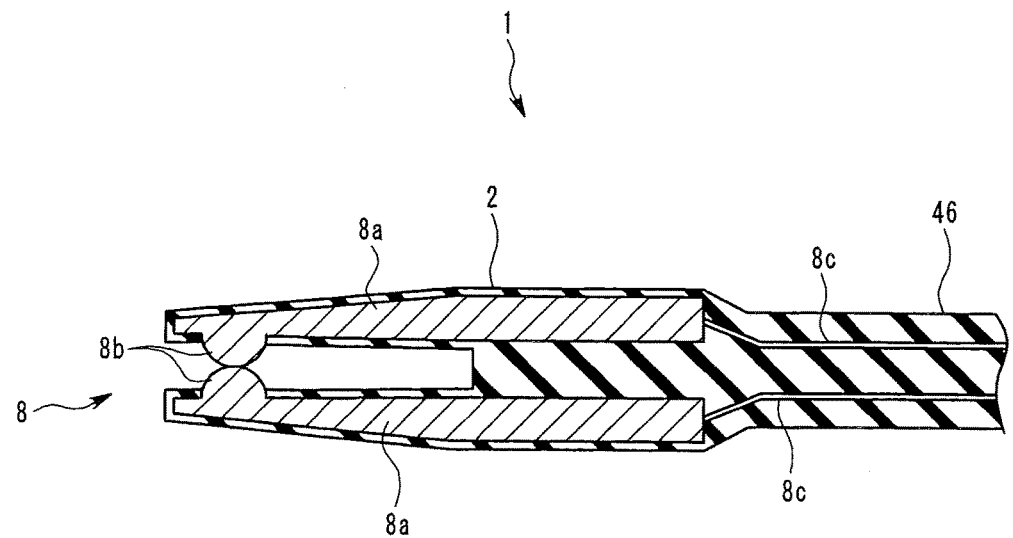
FIG. 19 is a diagram illustrating a state in which a switch section of the heat monitoring instrument according to the sixth embodiment has deformed.

When the temperature of the switch section 8 exceeds the predetermined temperature Th and the insulating member 8d melts or softens, as illustrated in FIG. 19, the pair of electrodes 8b are brought into contact with each other by biasing forces of the plate springs 8a. In other words, the switch section 8 deforms when the temperature thereof exceeds the predetermined temperature Th and thereby provides conduction between the pair of electrodes 8b.

In an ablation method using the heat monitoring instrument 1 and the drive apparatus 21 configured as described above, in a step IV, checking of whether or not deformation of the switch section 8 provided in the insertion portion 2 and stoppage of the ablation instrument 20 can automatically be performed, enabling reduction in burden on the surgeon.

In the present embodiment, also, as in the first, third, fourth and fifth embodiments, a surgeon can easily and reliably check change in temperature of a tissue at a desired position when ablation is performed, using the heat monitoring instrument 1. Also, since whether or not deformation of the heat monitoring instrument 1 occurs can be checked without using an ultrasound tomographic image, which is a two-dimensional image, a surgeon can see the state of thermal change of a tissue at a position not visualized in the ultrasound tomographic image during operation of the ablation instrument 20.

Furthermore, the heat monitoring instrument 1 has a simple structure and is thus inexpensive, enabling reduction of costs for ablation.

It should be understood that the present embodiment is not limited to the above-described embodiments, and various modifications and applications are possible without departing from the spirit of the invention. Furthermore, the above-described embodiments include inventions of various phases, and various inventions may be extracted by proper combinations of the plurality of elements disclosed.

What is claimed is:

1. An ablation method comprising:
   a step I of observing an ablation target region in a tissue of a subject and a conservation region that should not be ablated, the conservation region being adjacent to the ablation target region, using observation means;
   a step II of placing a heat monitoring instrument that deforms if a temperature thereof exceeds a predetermined temperature, in a boundary between the ablation target region and the conservation region under the observation using the observation means, the heat monitoring instrument including a locking portion that engages with a tissue in the boundary when the temperature of the heat monitoring instrument is equal to or below the predetermined temperature, and deforms and thereby disengages from the tissue when the heat monitoring instrument is heated from the temperature that is equal to or below the predetermined temperature to a temperature exceeding the predetermined temperature;
   a step III of heating the ablation target region using an ablation instrument while observing the ablation target region using the observation means, a tensile force that pulls the heat monitoring instrument from the tissue toward an outside of a body of the subject being applied to the heat monitoring instrument; and
   a step IV of stopping the heating at a stage where deformation of the heat monitoring instrument is confirmed based on detection of reduction or loss of the tensile force applied to the heat monitoring instrument.

2. The ablation method according to claim 1, wherein the step III, the tensile force is applied to the heat monitoring instrument by a surgeon or an assistant for the surgeon via fingers thereof.

\* \* \* \* \*